United States Patent
Bannigan et al.

(10) Patent No.: US 11,826,078 B2
(45) Date of Patent: Nov. 28, 2023

(54) POST-OPERATIVELY ADJUSTABLE SPINAL FIXATION DEVICES

(71) Applicant: NuVasive, Inc., San Diego, CA (US)

(72) Inventors: Shaeffer Bannigan, San Diego, CA (US); Justin Doose, San Diego, CA (US)

(73) Assignee: Nuvasive Inc., San Diego, CA (US)

( * ) Notice: Subject to any disclaimer, the term of this patent is extended or adjusted under 35 U.S.C. 154(b) by 0 days.

(21) Appl. No.: 17/707,269

(22) Filed: Mar. 29, 2022

(65) Prior Publication Data

US 2022/0280198 A1  Sep. 8, 2022

Related U.S. Application Data

(63) Continuation of application No. 16/363,090, filed on Mar. 25, 2019, now Pat. No. 11,291,478, which is a continuation-in-part of application No. 15/432,647, filed on Feb. 14, 2017, now abandoned, which is a continuation of application No. PCT/US2017/017700, filed on Feb. 13, 2017.

(60) Provisional application No. 62/294,975, filed on Feb. 12, 2016.

(51) Int. Cl.
*A61B 17/70* (2006.01)
*A61B 17/00* (2006.01)

(52) U.S. Cl.
CPC ...... *A61B 17/7016* (2013.01); *A61B 17/7043* (2013.01); *A61B 17/7052* (2013.01); *A61B 17/7053* (2013.01); *A61B 2017/00876* (2013.01)

(58) Field of Classification Search
CPC .................. A61B 17/7053; A61B 17/7016
See application file for complete search history.

(56) References Cited

U.S. PATENT DOCUMENTS

| | | |
|---|---|---|
| 5,180,393 A | 1/1993 | Commarmond |
| 5,375,823 A | 12/1994 | Navas |
| 5,387,213 A | 2/1995 | Breard |
| 5,611,800 A * | 3/1997 | Davis ................. A61B 17/7037 606/250 |
| 5,628,756 A | 5/1997 | Barker, Jr. |
| 5,672,175 A | 9/1997 | Martin |
| 5,800,434 A | 9/1998 | Campbell, Jr. |
| 5,810,815 A | 9/1998 | Morales |
| RE36,221 E | 6/1999 | Breard |
| 6,296,643 B1 | 10/2001 | Hopf |
| 7,377,921 B2 | 5/2008 | Studer |
| 7,815,663 B2 | 10/2010 | Trieu |
| 8,057,472 B2 | 11/2011 | Walker |

(Continued)

OTHER PUBLICATIONS

International Search Report dated Aug. 17, 2017 for International Application No. PCT/US2017/017700, 5 pages.

(Continued)

*Primary Examiner* — Tessa M Matthews

(57) ABSTRACT

A system for spinal fixation with a non-rigid portion at least one of the caudal or cephalad terminus. Various devices and techniques are described for transition from a rigid fixation construct to a less rigid support structure applied to a "soft zone" that helps share the stress created on the spinal levels caused by the fixed levels below. In some embodiments, the soft zone is provided by terminating the construct with one of a flexible tether or a dampening rod.

14 Claims, 7 Drawing Sheets

(56) References Cited

U.S. PATENT DOCUMENTS

| | | |
|---|---|---|
| 8,197,490 B2 | 6/2012 | Pool |
| 8,337,528 B2 | 12/2012 | Ferree |
| 8,343,192 B2 | 1/2013 | Kiester |
| 8,382,756 B2 | 2/2013 | Pool |
| 8,414,614 B2 | 4/2013 | Firkins |
| 8,419,734 B2 | 4/2013 | Walker |
| 8,419,773 B2 | 4/2013 | Biedermann |
| 8,449,543 B2 | 5/2013 | Pool |
| 8,523,922 B2 | 9/2013 | May |
| 8,617,214 B2 | 12/2013 | Malek |
| 8,685,026 B2 | 4/2014 | Carls |
| 8,715,159 B2 | 5/2014 | Pool |
| 8,734,488 B2 | 5/2014 | Pool |
| 8,801,757 B2 | 8/2014 | Abdou |
| 8,852,187 B2 | 10/2014 | Pool |
| 8,852,236 B2 | 10/2014 | Kiester |
| 8,974,463 B2 | 3/2015 | Pool |
| 9,011,499 B1 | 4/2015 | Kiester |
| 9,107,706 B2 * | 8/2015 | Alamin ............... A61B 17/7064 |
| 9,179,938 B2 | 11/2015 | Pool |
| 9,179,960 B2 | 11/2015 | Walker |
| 9,186,183 B2 | 11/2015 | Pool |
| 9,198,755 B2 | 12/2015 | Shaolian |
| 9,220,541 B1 | 12/2015 | Dant |
| 9,757,159 B2 | 9/2017 | Pool |
| 9,770,274 B2 | 9/2017 | Pool |
| 9,848,914 B2 | 12/2017 | Pool |
| 10,016,220 B2 * | 7/2018 | Culbert ............... A61B 17/863 |
| 11,291,478 B2 | 4/2022 | Bannigan et al. |
| 2006/0058790 A1 | 3/2006 | Carl |
| 2006/0058792 A1 * | 3/2006 | Hynes ............... A61B 17/8685 |
| | | 606/258 |
| 2007/0088359 A1 * | 4/2007 | Woods ............... A61B 17/7028 |
| | | 606/86 A |
| 2008/0281361 A1 * | 11/2008 | Vittur ............... A61B 17/7052 |
| | | 606/249 |
| 2009/0012565 A1 | 1/2009 | Sachs |
| 2009/0216276 A1 | 8/2009 | Pasquet |
| 2009/0222042 A1 | 9/2009 | Firkins |
| 2010/0217271 A1 * | 8/2010 | Pool ............... A61B 17/7016 |
| | | 606/264 |
| 2012/0109202 A1 | 5/2012 | Kretzer |
| 2012/0130428 A1 | 5/2012 | Hunziker |
| 2013/0072983 A1 | 3/2013 | Lindquist |
| 2013/0123854 A1 | 5/2013 | Kondrashov |
| 2013/0218207 A1 | 8/2013 | Carls |
| 2014/0031870 A1 | 1/2014 | Chang |
| 2014/0180297 A1 | 6/2014 | Jamshidi |
| 2014/0236234 A1 * | 8/2014 | Kroll ............... A61B 17/7016 |
| | | 606/279 |
| 2014/0296918 A1 | 10/2014 | Fening |
| 2015/0105826 A1 * | 4/2015 | Green ............... A61B 17/7055 |
| | | 606/263 |
| 2016/0066962 A1 | 3/2016 | Dant |
| 2016/0346016 A1 | 12/2016 | Northcutt |
| 2017/0014171 A1 | 1/2017 | Alamin |
| 2017/0231661 A1 | 8/2017 | Bannigan |
| 2018/0078286 A1 | 3/2018 | Le Couedic |
| 2019/0167314 A1 * | 6/2019 | Mosnier ............. A61B 17/7076 |
| 2022/0151662 A1 * | 5/2022 | Murray ............... A61B 17/705 |
| 2022/0323119 A1 * | 10/2022 | Berry ............... A61B 17/7062 |

OTHER PUBLICATIONS

Written Opinion of the International Searching Authority dated Aug. 17, 2017 for International Application No. PCT/US2017/017700, 12 pages.

* cited by examiner

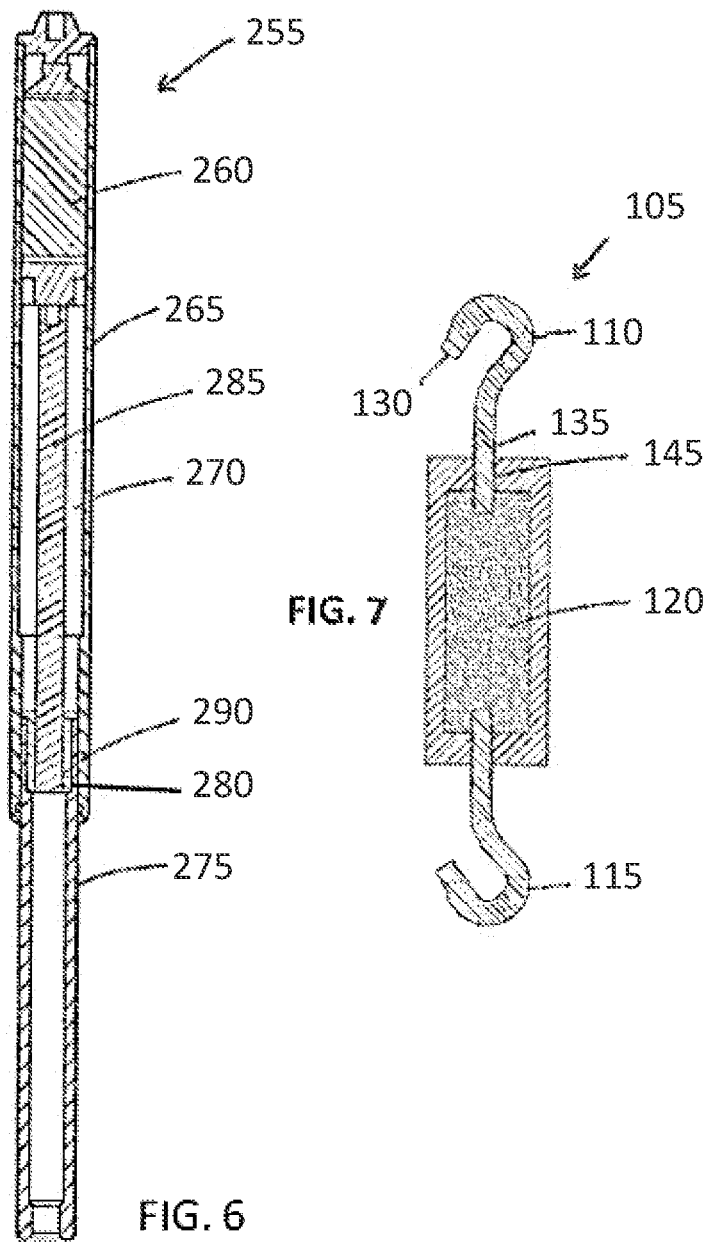

POST-OPERATIVELY ADJUSTABLE SPINAL FIXATION DEVICES

CROSS-REFERENCES

This application is a continuation of U.S. patent application Ser. No. 16/363,090, filed Mar. 25, 2019, which is a continuation-in-part of U.S. patent application Ser. No. 15/432,647, filed Feb. 14, 2017, now abandoned, which is a continuation of International Application PCT/US17/17700, filed Feb. 13, 2017, which claims priority to U.S. Patent Application No. 62/294,975, filed Feb. 12, 2016. The entire contents of all these applications are hereby incorporated by reference.

BACKGROUND

Field

The present disclosure relates generally to medical devices, and specifically to surgical instruments and methods for performing spinal procedures.

The spine is critical in human physiology for mobility, support, and balance. The spine protects the nerves of the spinal cord, which convey commands from the brain to the rest of the body, and convey sensory information from the nerves below the neck to the brain. Even minor spinal injuries can be debilitating to the patient, and major spinal injuries can be catastrophic. The loss of the ability to bear weight or permit flexibility can immobilize the patient. Even in less severe cases, small irregularities in the spine can put pressure on the nerves connected to the spinal cord, causing devastating pain and loss of coordination.

The spinal column is a bio-mechanical structure composed primarily of ligaments, muscles, bones, and connective tissue that forms a series of vertebral bodies stacked one atop the other and intervertebral discs between each vertebral body. The spinal column provides support to the body and provides for the transfer of the weight and the bending movements of the head, trunk and arms to the pelvis and legs; complex physiological motion between these parts; and protection of the spinal cord and the nerve roots.

The stabilization of the vertebra and the treatment for spinal conditions may be aided by a surgically implanted fixation device which holds the vertebral bodies in proper alignment and reduces the patient's pain and prevents neurologic loss of function. Spinal fixation is a frequently used medical procedure. Spinal fixation systems can be surgically implanted into a patient to aid in the stabilization of a damaged spine or to aid in the correction of other spinal deformities. Existing systems can use a combination of rods, plates, pedicle screws, bone hooks, locking screw assemblies, and connectors, for fixing the system to the affected vertebrae. The system components may be rigidly locked together to fix the connected vertebrae relative to each other, stabilizing the spine until the bones can fuse together.

Whatever the treatment, the goal remains to improve the quality of life for the patient. In some instances, patients who receive implants to treat the primary pathology develop a secondary condition called junctional disease. The junctional disease can occur at the proximal or cephalad area of spinal instrumentation and is then termed "adjacent segment pathology." Clinical Adjacent Segment Pathology (CASP) refers to clinical symptoms and signs related to adjacent segment pathology. Radiographic Adjacent Segment Pathology (RASP) refers to radiographic changes that occur at the adjacent segment. A subcategory of CASP and RASP that occurs at the proximal end of the instrumentation is termed proximal junctional kyphosis (PJK). PJK may be defined in several manners and commonly is specified as kyphosis measured from one segment cephalad to the upper end instrumented vertebra to the proximal instrumented vertebra with abnormal value defined as 10° or greater. In practice, this can often mean that the patient's head and/or shoulders may tend to fall forward to a greater degree than should normally occur. Sometimes the degree is significant.

Adjacent segment pathology can occur as either a degenerative, traumatic or catastrophic condition and sometimes as a result from a combination of factors. Degenerative conditions are ones that occur over a period of time, normally 5 or 6 years but can occur at an accelerated rate particularly with altered mechanics related to spinal fusion. As a result, the patient's head and/or shoulder region(s) may fall forward gradually over time. Traumatic and catastrophic conditions may occur as a generally sudden shifting of the vertebral body immediately cephalad to the upper end instrumented vertebra and can lead to sudden changes in spinal alignment with marked symptoms noted by the patient.

Whether the condition is degenerative, traumatic, or catastrophic, the exact cause of adjacent segment pathology can be uncertain. Adjacent segment pathology and more specifically PJK can be a result of excess strain and stress on the proximal instrumented spinal segment which is then at least partially transferred to the bone structures, disc, ligaments and other soft tissues, causing a loss of normal structural integrity and mechanical properties. The resultant effect can be a forward (i.e., kyphotic) shift of the adjacent non-instrumented vertebral body. One such theory is that this strain and stress can be caused by suboptimal alignment and/or balance of the screw and rod construct. Another theory is that the rigidity of the screw and rod construct causes the problem in that the transition from a motion-restrained segment to a motion-unrestrained segment is too much for the non-instrumented (unrestrained) segment to handle over time. Yet another theory speculates that the specific level at which the proximal instrumented vertebra is located is of vital importance in that some levels may be better suited to handle a proximal termination of a fixation construct than others.

Thus there remains an urgent need for improvements and new systems for spinal fixation with at least a specific goal of preventing the occurrence of or reducing the degree of adjacent segment pathology and failures occurring at the distal junction (DJK), proximal junction (PJK), or both. The devices, implants, methods and techniques described herein are directed towards overcoming these challenges and others associated with spinal fixation.

SUMMARY OF THE INVENTION

The problems noted above, as well as potentially others, can be addressed in this disclosure by a system for spinal fixation with a non-rigid portion, e.g., a soft zone, at one or more of the caudal or cephalad terminus. Various devices and techniques are described herein for transition from a rigid fixation device to a less rigid, more flexible support structure applied to a "soft zone" that may help share the stress created on the spinal levels caused by the fixed levels below and/or above. In some embodiments, the soft zone is provided by terminating the spinal fixation system with one or more of a flexible tether assembly, a telescoping rod, or a dampening rod.

In a first aspect, a system for spinal fixation is provided comprising: a first bone anchor, anchored to a first vertebra in a subject, the first bone anchor comprising a first bone fastener attached to a first rod housing; a rigid spinal rod seated in the first rod housing to restrict translation of the rigid spinal rod relative to the first bone anchor; a second bone anchor, anchored to a second vertebra in the subject, the second bone anchor comprising a second bone fastener attached to a second rod housing, wherein the rigid spinal rod is seated in the second rod housing to restrict translation of the rigid spinal rod relative to the second bone anchor; and a compressible spinal connector, connected to the first or second bone anchor, and anchored to a third vertebra in the subject, the compressible spinal connector comprising a modulation mechanism for modulating at least one of the tension on the compressible spinal connector or the resistance to compression of the compressible spinal connector, wherein said modulation occurs in response to a remote signal.

In a second aspect, a spinal tether assembly for providing non-rigid intervertebral support is provided, comprising: a flexible tether; and an adjustable tensioner connected to exert tension on the flexible tether, the adjustable tensioner comprising a first magnet mounted to rotate in response to a spinning magnetic field; and a tensioning mechanism configured to convert rotation of the magnet to a decrease or increase of tension on the flexible tether, depending on the direction of the first magnet's rotation.

In a third aspect, a dampening spinal rod to adjust friction against tension and compression is provided, comprising: an elongate rigid portion for insertion into a bone anchor; a flared portion for receiving a terminal end of a second spinal rod, the flared portion comprising a rod cavity of sufficient diameter to accept the second spinal rod, and a friction control mechanism configured to modulate friction between the second spinal rod and said dampening spinal rod in response to a remote signal.

In a fourth aspect, a method of fixing the relative positions of a first vertebra and a second vertebra in a subject is provided, the method comprising: anchoring a first bone anchor to the first vertebra, the first bone anchor comprising a first bone fastener attached to a first rod housing; seating a rigid spinal rod in the first rod housing to restrict translation of the rigid spinal rod relative to the first bone anchor; anchoring a second bone anchor to the second vertebra, the second bone anchor comprising a second bone fastener attached to a second rod housing, seating the rigid spinal rod in the second rod housing to restrict translation of the rigid spinal rod relative to the second bone anchor; connecting a compressible spinal connector to the second bone anchor, the compressible spinal connector comprising a modulation mechanism for modulating at least one of the tension on the compressible spinal connector or the resistance to compression of the compressible spinal connector, wherein said modulation occurs in response to a remote signal; anchoring the compressible spinal connector to a third vertebra in the subject; and transmitting the remote signal to the modulation mechanism post-operatively, to cause said modulation to occur.

In another aspect, disclosed herein is a system for spinal fixation, the system comprising: a first bone anchor anchored to a first vertebra of a subject, the first bone anchor comprising a first bone fastener attached to a first rod housing; a second bone anchor anchored to a second vertebra in the subject, the second bone anchor comprising a second bone fastener attached to a second rod housing; a rigid spinal rod seated in the first rod housing to restrict translation of the rigid spinal rod relative to the first bone anchor and in the second rod housing to restrict translation of the rigid spinal rod relative to the second bone anchor; and a compressible spinal connector, connected to the rigid spinal rod and anchored to a third vertebra in the subject, the compressible spinal connector modulates, in response to a signal external to the system, at least one of: tension on the compressible spinal connector; or resistance to compression of the compressible spinal connector. In some cases, the signal is a magnetic field. In some cases, at least one of the first bone anchor, the second bone anchor, the rigid spinal rod, and the compressible spinal connector comprises a non-absorbable biocompatible material that is non-ferromagnetic. In some cases, the compressible spinal connector comprises a tether assembly. In some cases, the tether assembly comprises a first flexible tether at least partially wrapped around a structure of the third vertebra and connected to the rigid spinal rod to exert tension between the third vertebra and the rigid spinal rod. In some cases, the compressible spinal connector comprises an adjustable tensioner configured to vary the tension on the first flexible tether. In some cases, the first flexible tether is constructed of a non-absorbable biocompatible material. In some cases, the tether assembly comprises a second flexible tether encircling the structure or a second structure of the third vertebra and a third structure of a fourth vertebra, and wherein the compressible spinal connector comprises an adjustable tensioner configured to vary the tension on the second flexible tether. In some cases, the adjustable tensioner comprises a turnbuckle comprising a threaded first end coupler, a second end coupler, and a rotatable magnet that rotates in response to a magnetic field, and wherein the rotatable magnet is connected to the threaded first end coupler to cause the threaded first end coupler to rotate about its longitudinal axis when the rotatable magnet rotates. In some cases, the adjustable tensioner comprises a spool about which the flexible tether is wound, and wherein rotation of a spool magnet drives rotation of the spool. In some cases, the adjustable tensioner comprises a locking mechanism configured to maintain tension on the flexible tether when engaged. In some cases, the compressible spinal connector comprises a dampening spinal rod that is compressible and expandable. In some cases, the dampening spinal rod comprises: an elongate rigid portion for insertion into a bone anchor; a flared portion for receiving a terminal end of a second elongate rigid portion, the flared portion comprising a rod cavity of diameter sufficient to accept the second elongate rigid portion. In some cases, the compressible spinal connector comprises a friction brake configured to vary the resistance of the dampening rod to the compression or the tension. In some cases, the friction brake comprises a set screw in a threaded channel positioned to exert compressive force on a spring, said spring positioned to exert compressive force against both the compression and tension of the dampening rod. In some cases, the set screw is magnetic and rotates in the threaded, channel in response to a magnetic field. In some cases, the compressible spinal connector comprises a telescoping spinal rod positioned within the second rod housing, wherein the telescoping spinal rod comprises: a rod magnet configured to rotate when exposed to a magnetic field and cause the telescoping spinal rod to either extend or collapse depending on a direction of the magnetic field; a first elongate element containing a cavity; and a second elongate element dimensioned to at least partially fit within the cavity, and having an internally threaded region, wherein the compressible spinal connector comprises a lead screw coupled to rotate when the rod magnet rotates, and comprising an externally threaded region engaged to the internally threaded region of the second elongate element, such that rotation of the lead screw causes the second elongate element to translate relative to the first elongate element. In some cases, a second rigid spinal rod is seated in an additional rod housing of an additional bone anchor that is anchored in at least one of the first and second vertebrae. In some cases, a transverse connector is fastened to the first rigid spinal rod and the second rigid spinal rod. In some cases, the vertebral fixation system herein further comprises: a third bone anchor comprising a third bone fastener and a third rod housing, anchored to the first vertebra; a fourth bone anchor, comprising a fourth bone fastener and a fourth rod housing, anchored to the second vertebra; a second rigid spinal rod seated in the third rod housing and the fourth rod housing, wherein the compressible spinal connector comprises: a first flexible tether at least partially wrapped around a structure of the third vertebra and connected to the first and second rigid spinal rods to exert tension between the third vertebra and the first and second rigid spinal rods, and a second flexible tether encircling the structure of the third vertebra and a second process of a fourth vertebra, wherein the compressible spinal connector comprises an adjustable tensioner connected to the first and second rigid spinal rods and the first or second flexible tethers, the adjustable tensioner comprising a magnet mounted to rotate in response to a magnetic field thereby increasing or decreasing tension on the first or second flexible tether depending on a direction of rotation of the magnet.

In another aspect, disclosed herein a system for spinal fixation comprising: a first bone anchor anchored to a first vertebra of a subject, the first bone anchor comprising a first bone fastener attached to a first rod housing; a second bone anchor anchored to a second vertebra in the subject, the second bone anchor comprising a second bone fastener attached to a second rod housing; a third bone anchor comprising a third bone fastener and a third rod housing, anchored to the first vertebra; a fourth bone anchor, comprising a fourth bone fastener and a fourth rod housing, anchored to the second vertebra; a rigid spinal rod seated in the first rod housing to restrict translation of the rigid spinal rod relative to the first bone anchor and in the second rod housing to restrict translation of the rigid spinal rod relative to the second bone anchor; a second rigid spinal rod seated in the third rod housing and the fourth rod housing, a compressible spinal connector, connected to the rigid spinal rod and anchored to a third vertebra in the subject, the compressible spinal connector modulates, in response to a signal external to the system, at least one of: tension on the compressible spinal connector; or resistance to compression of the compressible spinal connector, wherein the compressible spinal connector comprises: a first flexible tether at least partially wrapped around a structure of the third vertebra and connected to the first and second rigid spinal rods to exert tension between the third vertebra and the first and second rigid spinal rods, and a second flexible tether encircling the structure of the third vertebra and a second process of a fourth vertebra, and wherein the compressible spinal connector comprises a magnet mounted to rotate in response to a magnetic field thereby increasing or decreasing tension on the first or second flexible tether depending on a direction of rotation of the magnet.

In yet another aspect, disclosed herein is a system for spinal fixation comprising: a compressible spinal connector connected to a rigid spinal fixation rod implanted in a subject and anchored to a vertebra that is movable relative to the rigid spinal fixation rod, wherein the compressible spinal connector comprises: a first flexible tether at least partially wrapped around a structure of the vertebra and connected to the rigid spinal rod to exert tension between the vertebra and the rigid spinal rod; and a second flexible tether encircling the structure or a second structure of the vertebra and a third of a second vertebra; and a magnet mounted to rotate in response to an external magnetic field thereby increasing or decreasing tension on the first or second flexible tether depending on a direction of rotation of the magnet.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 6 shows a cross-sectional view of an exemplary embodiment of a telescoping spinal rod of the vertebral fixation system disclosed herein;

FIG. 7 shows an exemplary embodiment of a turnbuckle tensioner for modulating the tension on a flexible tether of the vertebral fixation system disclosed herein;

DETAILED DESCRIPTION

Figure 1:
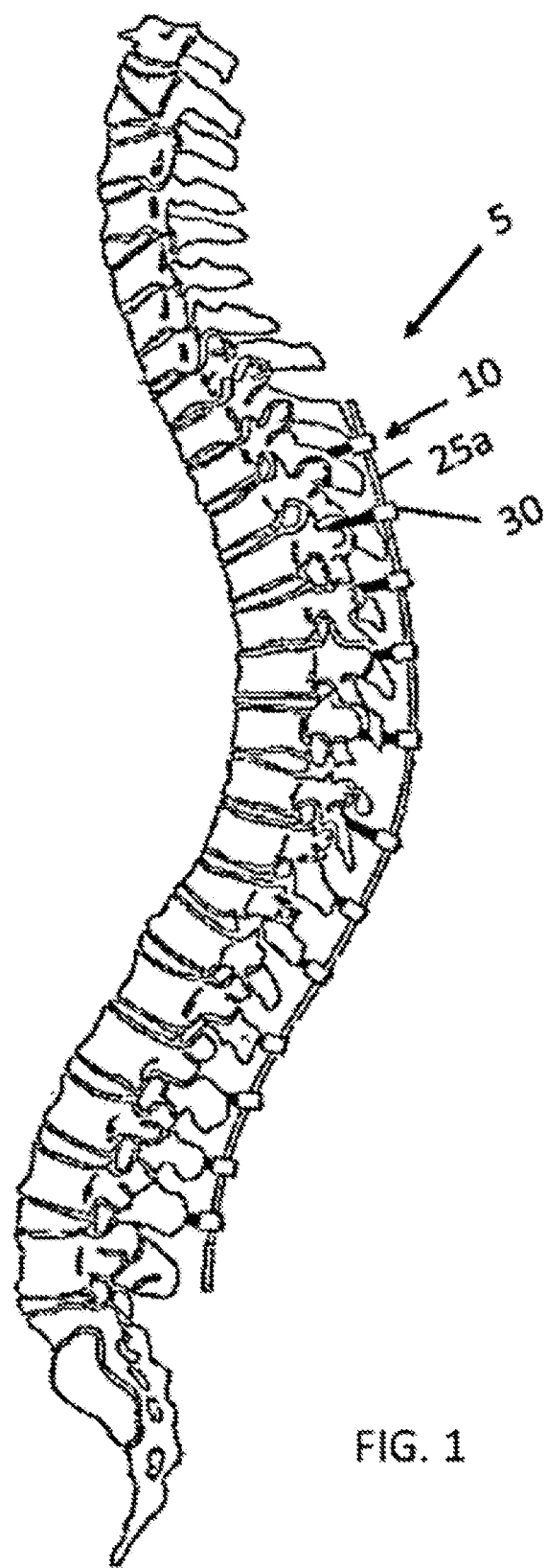
FIG. 1 shows an example of a vertebral fixation system disclosed herein, in accordance with embodiment(s) disclosed herein.

Illustrative embodiments of a system for spinal fixation, parts, and methods for use thereof, are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The system for spinal fixation, parts, and methods for use thereof disclosed herein boasts a variety of inventive features and components that warrant patent protection, both individually and in combination.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated. As used in this specification and the appended claims, "about," or "approximately" indicate ±0.1 to ±15% difference from the subject matter that is being characterized. As a nonlimiting example, about 90 degrees may indicate 89.5 degrees, 88 degrees, 100 degrees, or any number(s) in the range from 75 degrees to 105 degrees.

As disclosed herein, "caudal" is equivalent to "distal" and "cephalad" is equivalent to "proximal."

The present disclosure includes a variety of transitional or terminal components that may be implanted or otherwise used as part of a vertebral fixation system disclosed herein, equivalently as a spinal fixation system. In some embodiments, the vertebral fixation systems disclosed herein is to decrease the potential for subsequent development of junctional disease or failure, for example, subsequent to a spinal surgical procedure. In the examples shown, only the cephalad most level (for terminal hardware) or levels (for multi-level transitional hardware) of the fixation system (e.g., those utilizing the exemplary components described herein) are illustrated. It should be appreciated, however, that the entire vertebral fixation system may extend any number of levels from a single level construct to a long construct spanning multiple spinal levels and multiple spinal regions from the lumbosacral to cervical regions (such as the exemplary embodiment illustrated in FIG. 1), and/or with any variety of combinations of known anchors, rods, and connectors. It should also be appreciated that the exemplary terminal and/or transitional components may additionally or alternatively be utilized at the caudal or distal end of the fixation construct. In some embodiments, the vertebral fixation systems described herein is used along any aspect of the spine (e.g., anterior, posterior, antero-lateral, postero-lateral). In some embodiments, the vertebral fixation systems are particularly suited for implantation along a posterior aspect of the spine.

In some embodiments, the vertebral fixation system disclosed herein comprises a first bone anchor, anchored to a first vertebra in a subject, the first bone anchor comprising a first bone fastener attached to a first rod housing. A rigid spinal rod can be seated in the first rod housing to restrict translation of the rigid spinal rod relative to the first bone anchor. The rigid spinal rod can also be seated in the rod housing of a second bone anchor, anchored to a second vertebra in the subject, so as to restrict translation of the rigid spinal rod relative to the second bone anchor. A compressible spinal connector can be connected to the first and/or second bone anchor and anchored to a third vertebra in the subject. The compressible spinal connector, may have a modulation mechanism for modulating either the tension on the compressible spinal connector or its resistance to compression (or both), thereby allowing adjustment between the second bone anchor and the third vertebrae. The modulation can occur in response to a signal external to the vertebral fixation system. Consequently, modulation of the tension and/or resistance to compression may not require access to the vertebral fixation system through the patient's tissues, and may be performed post-operatively. The external, remote signal may be, for example, an electromagnetic signal. A specific example of the remote, external signal is a spinning magnetic field.

FIG. 1 illustrates an exemplary embodiment of the vertebral fixation systems. In this particular embodiment, the illustrated vertebral fixation system 5 is a screw-and-rod construct adapted for implantation along the posterior aspect of the human spinal column. In this particular embodiment, the vertebral fixation system 5 includes a pair of elongate rods 25a, 25b (one rod shown) dimensioned to span multiple vertebral levels and a plurality of bone anchors, e.g., 10, 30. The bone anchors can be threaded bone anchors and/or hook-type bone anchors. The vertebral fixation system can also include a plurality of transverse connectors or cross connectors dimensioned to rigidly engage each of the elongate rods 25a, 25b so as to hold each rod in place relative to the other. The transverse connectors or cross connectors may be provided as fixed connectors or adjustable connectors, in any quantity that is required by the surgeon performing the implantation surgery.

It is contemplated that any of the examples of bone anchors and other transition structures or elements of the vertebral fixation systems described herein may be substituted for the cephalad bone anchors and/or caudal bone anchors which are traditionally rigid and identical to the other bone anchors used throughout the system. It is also contemplated that the examples of flexible or compressible spinal connectors, adjustable connectors, any other structure/elements described herein may replace existing hardware at the cephalad and/or caudal terminus of the traditional vertebral fixation system such that there is no additional surgical footprint realized. It is further contemplated that the examples of the vertebral fixation system and its structure elements described herein may augment existing hardware at the cephalad and/or caudal terminus of the traditional vertebral fixation system such that there is additional added surgical footprint realized. This may be applicable with the various embodiments that can be installed with minimal disruption of additional muscle tissue and/or ligament structure. Junctional disease or failure can be a problem at either the cephalad or caudal terminus (or both) of vertebral fixation systems. Therefore, although the various examples disclosed herein may be described in terms of cephalad terminus and proximal joint disease (for ease of disclosure) it is to be understood that any of the example embodiments are also applicable and may be used at the caudal terminus and distal joint disease of the vertebral fixation system without deviating from the scope of this disclosure.

According to one example, a spinal fixation system 5, like that shown in FIG. 1, is applied to the spinal levels to be fixed. Above the fixed levels or the fixed zone, a soft-zone can be created by applying non-rigid support elements such as tethers or adjustable rods that limit certain motion and reduce stress, to the levels of the soft-zone and above, while not inhibiting all motion. The tension applied to the support elements in the soft zone can be adjusted post-operatively and non-invasively to account for changing dynamics in the body, or for any other reason deemed desirable.

The components in the vertebral fixation system can be constructed from one or more non-absorbable biocompatible materials. Specific non-limiting examples of such suitable materials include titanium, alloys of titanium, steel, and stainless steel. Parts of the system can be made from non-metallic biocompatible materials, which include aluminum oxide, calcium oxide, calcium phosphate, hydroxyapatite, zirconium oxide, and polymers such as polypropylene. Interference with a magnetic field (e.g., the external signal) can be reduced by constructing one or more portions of the system from a nonmagnetic, non-ferromagnetic, or weakly magnetic material. Specific examples of such nonmagnetic non-absorbable biocompatible material include titanium, alloys of titanium, aluminum oxide, calcium oxide, calcium phosphate, hydroxyapatite, zirconium oxide, and polymers such as polypropylene. Examples of weakly magnetic materials include paramagnetic materials and diamagnetic materials. In a specific embodiment, the weakly magnetic material is austenitic stainless steel.

The first, second, and third vertebrae may be adjacent or non-adjacent to one another, in any combination. Thus it is contemplated that the first vertebra can be adjacent to the second, which can be adjacent to the third; the first vertebra can be nonadjacent to the second, which can be adjacent to the third; the first vertebra can be nonadjacent to the second, which can be nonadjacent to the third; and that the first vertebra can be adjacent to the second, which can be nonadjacent to the third.

Figure 3:
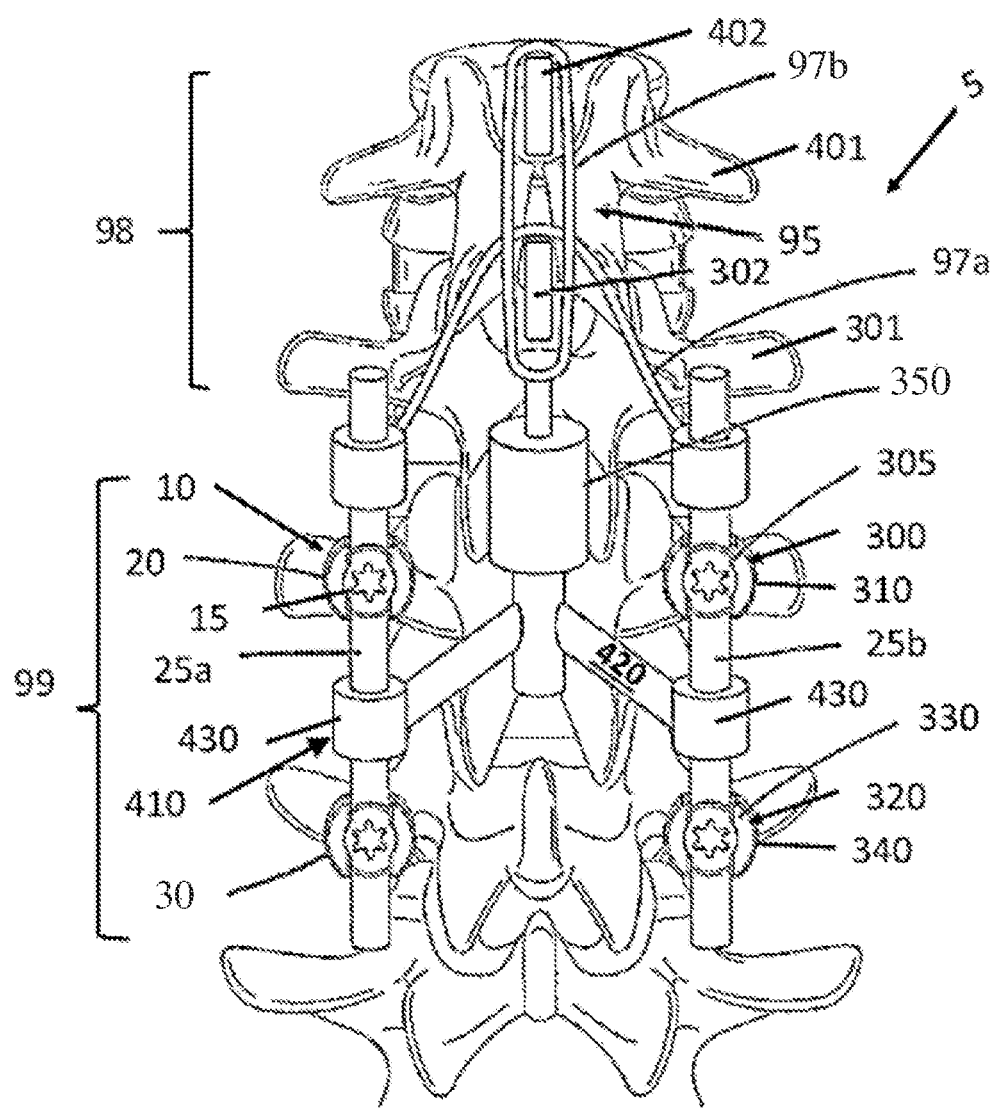
FIG. 3 shows a dorsal (posterior) view of an exemplary embodiment of the vertebral fixation system.

Referring to FIG. 3, in a particular embodiment, the vertebral fixation system 5 disclosed herein comprises a first bone anchor 10, anchored to a first vertebra in a subject, the first bone anchor comprising a first bone fastener (e.g., a threaded shank of the bone anchor) attached to a first rod housing 20. A set screw 15 may be used to lock the rod in the first rod housing. A rigid spinal rod 25a can be seated in the first rod housing 20 to restrict translation of the rigid spinal rod relative to the first bone anchor 10. The rigid spinal rod can also be seated in the rod housing of a second bone anchor 30, anchored to a second vertebra in the subject, so as to restrict translation of the rigid spinal rod 25a relative to the second bone anchor 30. A compressible spinal connector can be connected to the first or second bone anchor and anchored to a third vertebra 301 in the subject. In this particular embodiment, the vertebral fixation system 5 includes a compressible spinal connector including one or more tether assemblies 95. In the tether assembly 95, the modulation mechanism is an adjustable tensioner 350 configured to vary the tension on a flexible tether 97a. This may control the tension between the third bone anchor 300 and/or the first bone anchor 10 and the third vertebra 301. In this exemplary embodiment, the tethers 97a, 97b may be attached between the fixation hardware (e.g., bone anchor(s) and elongate rod(s)) and the soft-zone 98 (e.g., one or more non-fixed levels above), and/or directly between the bone elements of one or more fixed levels 99 and the soft-zone, and/or between two or more of the non-fixed levels in the soft-zone. As a nonlimiting example, a tether 97b may be wrapped around spinous processes of two vertebrae 302, 402 in the soft zone. As another example, a tether may be connected to a rigid spinal rod 25a or 25b and at least partly wrapped around a spinous process of one vertebra in the soft zone 302.

The tether 97a, 97b may be formed of any material suitable for medical use. For example, the tether may be made from allograft tendon, autograft tendon, braided, woven, or embroidered polyethylene, braided, woven, or embroidered polyester, polyether ether ketone (PEEK), or polyetherketoneketone (PEKK). In some instances, the tether 97a, 97b may be formed of elastic material.

FIG. 3 depicts multiple tethers 97a, 97b applied to the spine in the soft zone 98 adjacent to the fixed zone 99 and connected to the vertebral fixation system 5 by adjustable tensioner(s) 350. Nonlimiting examples of the adjustable tensioner, equivalently herein as the adjustable tension connector, include an adjustable tension tether-rod connector, an adjustable tension cross-connector shown in FIG. 8, a turnbuckle shown in FIG. 7, and a spool shown in FIG. 4. It will be appreciated that while shown in use together, either of these connectors may also be used on their own. and in any configuration desired. In use, once the tethers 97a, 97b are connected to the fixation system 5 and the tether(s) coupled to the desired bone structure (or other bone connection element) the tension on the tether(s) can be adjusted. Later, the tension on the tether can be adjusted post-operatively using an external device, e.g., 155 in FIG. 9, that controls the adjustable tensioners 350.

The vertebral fixation system disclosed herein and structure elements thereof may be unilateral, in which the network of bone anchors and rods is present on one side of the spine. The vertebral fixation system disclosed herein and structure elements thereof may be bilateral and is present on either side of the spine. Such a bilateral system may comprise a second rigid spinal rod 25b seated in an additional rod housing of an additional bone anchor that is anchored in at least one of the first and second vertebrae.

Continuing to refer to FIG. 3, in this embodiment, the system 5 comprises a third bone anchor 300 (comprising a third bone fastener and a third rod housing 310) anchored to the first vertebra, and a fourth bone anchor 320 (comprising a fourth bone fastener and a fourth rod housing 340) anchored to the second vertebra. The third bone anchor may further include a set screw 305 that lock the rod in the rod housing, similarly, the fourth bone anchor may further comprise a set screw 330. A second rigid spinal rod 25b is seated in the third rod housing 310 and the fourth rod housing 340, running substantially parallel to the first rod 25a. The compressible spinal connector can include an adjustable tether assembly 95 having a first flexible tether 97a at least partially wrapped around a spinous process of the third vertebra and connected to both of the first 25a and second rigid spinal rods 25b to exert tension between the third vertebra and the first 25a and second rigid spinal rods 25b. The adjustable tether assembly 95 may also include a second flexible tether 97b encircling the spinous process of the third vertebra 301 and a spinous process of a fourth vertebra 401. The compressible spinal connector can also include an adjustable tensioner 350 connected to the first 25a and second 25b rigid spinal rods. The adjustable tensioner 350 can include a magnet mounted to rotate in response to a spinning magnetic field, and a connection of the magnet to the tether(s) configured to increase or decrease the tension on the second flexible tether 97b depending on the direction of rotation of the magnet. In some embodiments, the tether(s) may be wrapped around or otherwise attached to any structure element of a vertebra other than the spinous process. The adjustable tensioner 350 extends or retracts the tether depending on the direction of the spinning magnetic field, either reducing or increasing the tension respectively.

Figure 8:
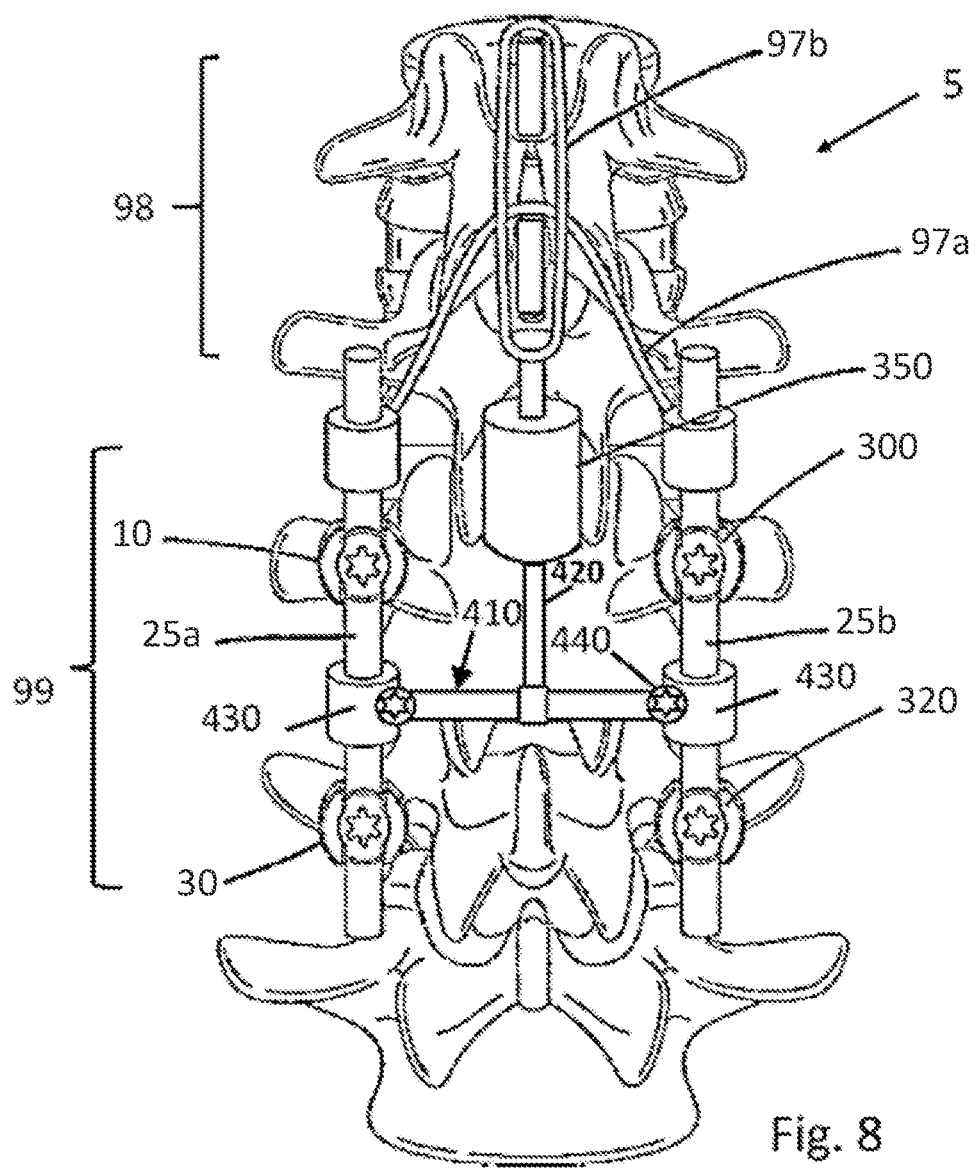
FIG. 8 shows a dorsal (posterior) view of an exemplary embodiment of the spinal fixation systems.

As shown in FIGS. 3 and 8, one or more transverse connectors or cross connectors 410 adjustably or fixedly fastened to the first rigid spinal rod 25*a* and the second rigid spinal rod 25*b* may be present for additional stability.

FIG. 3 shows an exemplary embodiment of the adjustable tension cross connector. In this embodiment, the adjustable tension cross connector 410 includes a pair of rod connectors 430 that couple and lock the adjustable tension cross connector to each of the rods 25*a*, 25*b*. Support arms 420 extends from the rod connector and supports the housing of the adjustable tensioner 350.

FIG. 8 shows another exemplary embodiment of the adjustable tension cross connector 410. In this particular embodiment and in the embodiment shown in FIG. 3, the adjustable tensioner connector may provide stability and rigidity to the elongate rods 25*a*, 25*b*. The adjustable cross-connector can be fixedly or adjustably anchored to the vertebra using elements such as bone anchors, for example, rod connectors 430, pedicle screws, set screws 440, and/or hooks. The adjustable cross-connector can hold the elongate rods 25*a*, 25*b* in a desired position. The adjustable cross-connector can connect to the adjustable tensioner via support arm(s) 420 thus provide support for the adjustable tensioner 350.

Referring to FIG. 7, in a particular embodiment, the adjustable tensioner includes a turnbuckle 105 comprising a threaded first end coupler 110, a second end coupler 115, and a rotatable magnet 120 that rotates in response to a spinning magnetic field and that is connected to the threaded first end coupler 110 to cause the threaded first end coupler 110 to rotate about its longitudinal axis when the rotatable magnet 120 rotates. FIG. 7 shows a cross-section of the turnbuckle 105 including a cylindrical magnet 125 oriented to rotate around its longitudinal axis when exposed to a spinning magnetic field in the right orientation. The threaded first end coupler 110 can be a hook 130 with a threaded shank 135. The threaded shank 135 runs through a threaded channel 140 in the housing 145 of the turnbuckle 105, which translates rotation of the shank 135 into translation of the hook 130. Alternatively, the magnet 125 itself may contain one or more threaded passages 150 that are engaged with the threaded shank(s) 135. As a result, the hook 130 can be extended or retracted by rotating the shank 135. In some embodiments of the turnbuckle, both end couplers 110, 115 are hooks with threaded shanks, the threads are oriented such that when the rotatable magnet rotates in a given direction the two hooks translate in opposite directions (i.e., they either converge or diverge along their shared longitudinal axis). When the hooks are caused to converge, it can increase tension on the connected spinal structure.

In some embodiments, the turnbuckle 105 can be attached to the spinous process or lamina of two vertebrae (either directly, or via tethers looped around the lamina or spinous process), and the tension between the vertebrae can be adjusted post-operatively and non-invasively using the external adjustment device to rotate the turnbuckle magnet 120. In some embodiments, such two vertebrae are adjacent to each other. In some embodiments, such two vertebrae are not adjacent to each other. Though shown only across a single level, turnbuckles 105 can be used at multiple levels. According to one example, the turnbuckles 105 can be used selectively to set the tension differently at each level. By way of example, the tension can start out higher closest to the fixed spinal levels, and be sequentially decreased over a series of levels through the soft-zone.

In some embodiments, a pair of turnbuckles is used bilaterally and coupled to tethers looped around the lamina and the superior and inferior coupled vertebrae. A distraction device can also be positioned between two spinous processes across a single level. It is contemplated that the distraction device can include a magnetically driven expansion device (such as one utilizing a lead screw coupled to a magnet, similar to that described below, to create linear expansion). This way, both flexion and extension can be effectively controlled, and adjusted post-operatively between two vertebrae. Taking it a step further, the addition of a rotatable element 220 within the disc to allow two adjacent vertebrae to rotate relative to each other, can facilitate scoliosis correction, e.g., in both the sagittal and coronal planes, using the adjustable turnbuckle 105 and distraction device(s).

Figure 4:
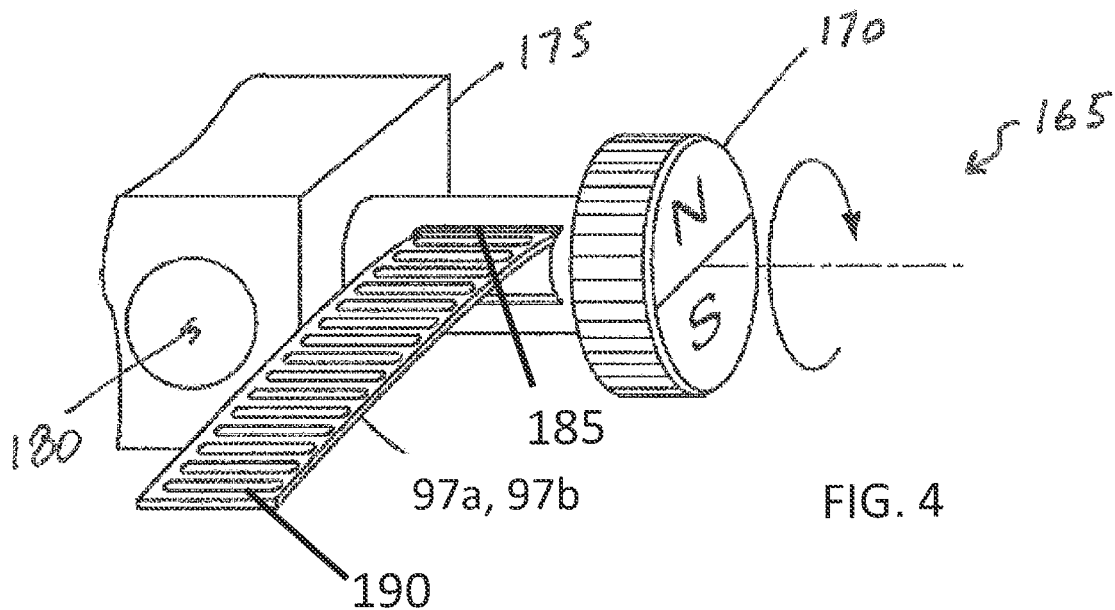
FIG. 4 shows a perspective view of an exemplary embodiment of a tensioner that modules the tension on a flexible tether of a vertebral fixation system disclosed herein.

One embodiment of the adjustable tensioner includes a spool about which the flexible tether is wound, and wherein rotation of a spool magnet drives rotation of the spool. An example of such an embodiment is shown in FIG. 4. In this particular embodiment, the spool 165 is connected to a body 175 having a rod passage 180 that couples to the rod 25*a*, 25*b*. A setscrew 205 or other element may be used to lock the body 175 to the rod 25*a*, 25*b*. The spool 165 is rotatably connected to the body 175. The tether 97*a*, 97*b* is attached to the spool 165 such that when the spool 165 rotates the tether 97*a*, 97*b* is wound up on the spool 165 to create tension. A first end 185 of the tether may be attached to the spool 165 with the second end 190 being otherwise attached to the target bone, another adjustable connector, or to itself (e.g. creating a loop that can be attached to the target bone, or both ends of the tether (185, 190) may be coupled to the spool 165 creating a loop to attach to or around the bone such that both ends of the tether (185, 190) are spooled up together). The spool magnet 170 can be driven by application of a magnetic field to rotate the spool 165. The spool magnet 170 may be a single cylindrical magnet poled north and south across its diameter to form two 180 degree sectors, as in FIG. 4. Alternatively, a quadrupole or multipole magnet may be used. The spool 165 may include a locking mechanism, such as a spool 165 and a ratchet mechanism, to maintain the tension applied. The locking mechanism may be externally controlled similar to the spool magnet 170 such that it can be locked and unlocked if adjustment is needed.

Figure 2:
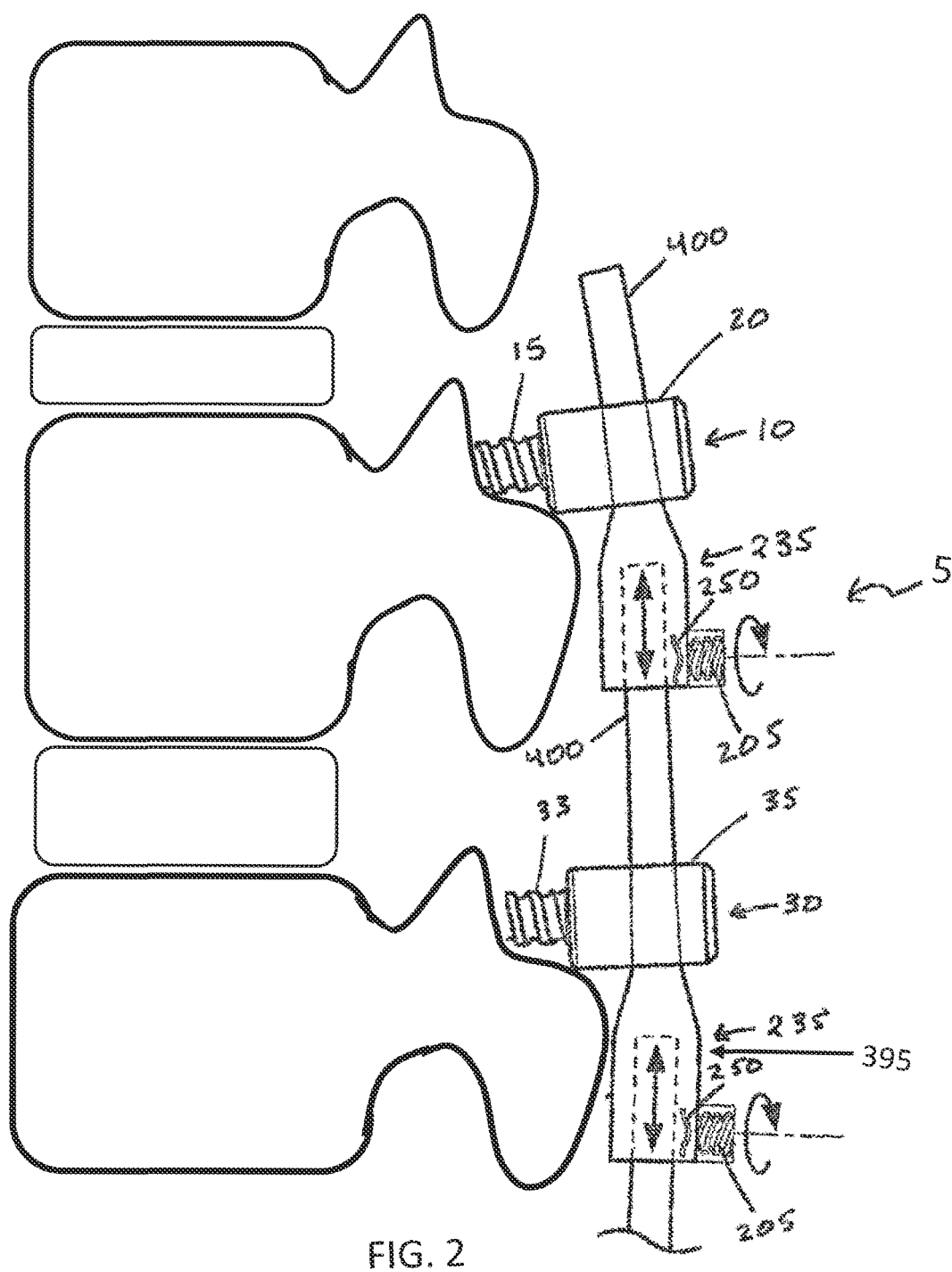
FIG. 2 shows a side view of an exemplary embodiment of the dampening spinal rod as part of a vertebral fixation system, in accordance with embodiment(s) disclosed herein.

According to one embodiment, the locking mechanism may be a set screw, e.g., 205 in FIG. 2, situated to inhibit rotation of the spool 165, when engaged. The set screw may be a magnetically driven set screw, oriented such that the external drive controller 155 can be positioned to drive only one of the set screw and drive magnet 230, and then prepositioned to drive the other. Alternatively, a locking pin or shaft could be advanced with the set screw to inhibit rotation of the spool 165.

Figure 5:
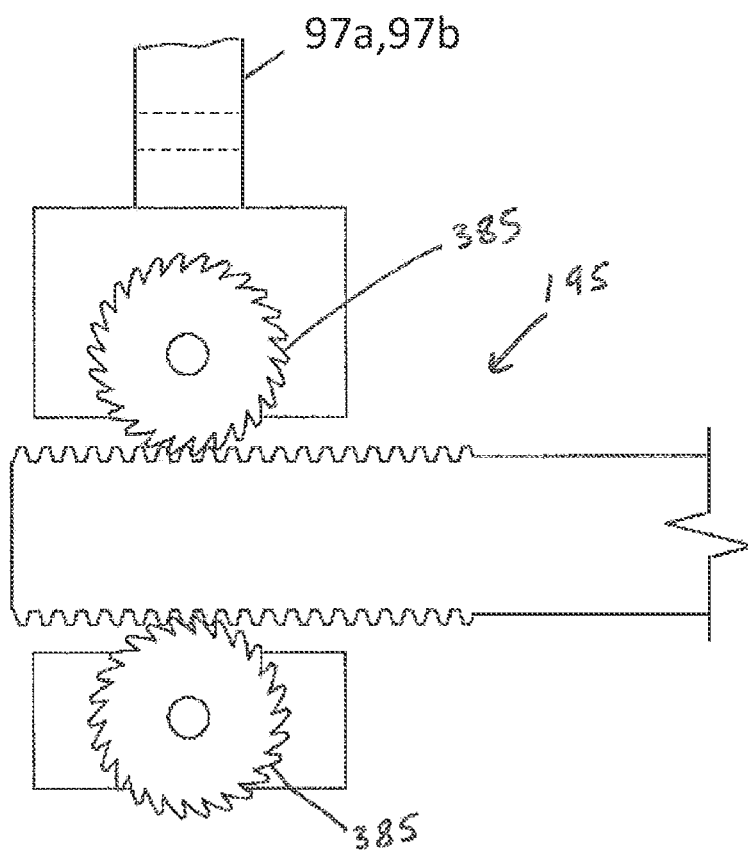
FIG. 5 shows an exemplary embodiment of a locking mechanism for locking a tensioner of the vertebral fixation system disclosed herein.
Figure 9:
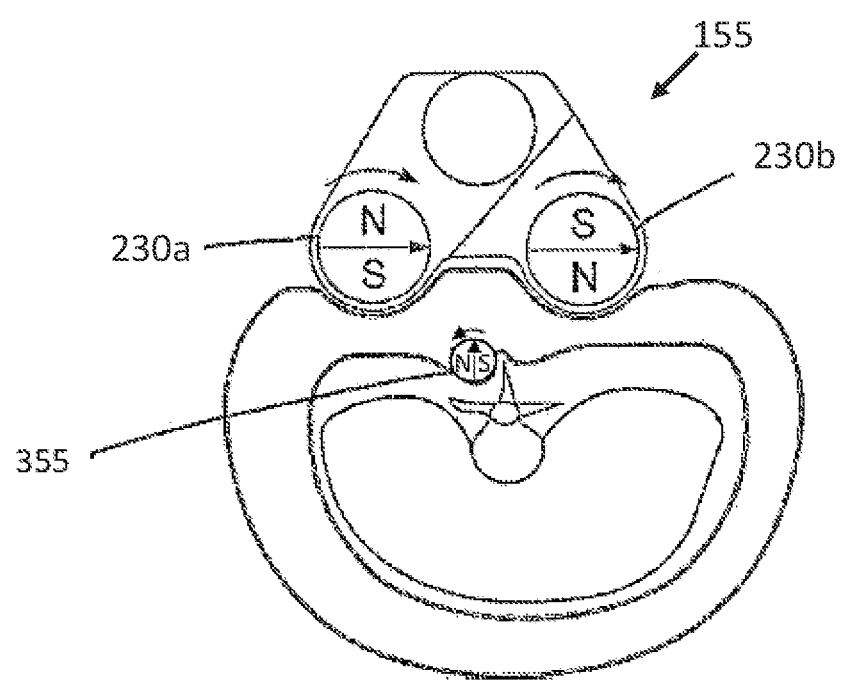
FIG. 9 shows a top view of an exemplary embodiment of the external control device of the vertebral fixation system disclosed herein.

In some embodiments, an external device 155, e.g., magnet 230*a*, 230*b* as in FIG. 9, may drive a gear assembly 380, as shown in FIG. 5, that rotates two opposing ratchet wheels 385 through which the tether 97*a*, 97*b* is passed, so that the tether may be locked when the gear assembly does rotate and unlocked when the gear assembly rotates.

In some embodiments, the compressible spinal connector herein includes a dampening rod. The dampening rod can be a rod that is both expandable and compressible, and the resistance to expansion and compression is controlled by means of the modulation mechanism herein. In some embodiments, the modulation mechanism includes a friction brake. The dampening rod can accommodate dynamic travel or length adjustment of the rod between the fixed connectors. The friction brake can include a set screw that is itself magnetic, or nonmagnetic itself but connected to a magnet ("brake magnet") that may be controllable via an external adjustment device. The degree of tension and support provided by the dampening rod can be controlled by increasing or decreasing friction with the set screw. Some embodiments of the friction brake can also lock down the rod entirely, to prevent any expansion or compression, should it later become necessary to fix one or more levels in the soft-zone. An embodiment of the dampening rod 235 is shown in FIG. 2. In this embodiment, each damping rod 235 has a wider bell region 395 and a narrower tail region 400. The tail 400 is about the diameter of an ordinary spinal rod. The bell 395 is open on the inside, and is dimensioned to accommodate a spinal rod (or the tail of another dampening rod 235). As shown in FIG. 2, the friction brake may be, for example, a set screw 205 in a threaded channel positioned to exert compressive force on a spring 250. The spring 250 can be positioned to exert compressive force against both the compression and expansion of the dampening rod 235. In this particular embodiment shown in FIG. 2, the spring 250 is positioned to exert compressive force on the tail portion 400 of an adjacent dampening rod 235. The spring 250 can be a wave spring, although other kinds of springs (e.g., helical) are contemplated as well. The set screw may be magnetic, or coupled to a magnet, such that a rotating magnetic field in the proper orientation may cause the set screw to rotate, either increasing or decreasing the compressive force that exerts the friction.

In some embodiments, the vertebral fixation system herein may be used together with a telescoping rod. As a nonlimiting example, the telescoping rod may be implanted at levels above a vertebral fixation system, e.g., in patients that are at high risk of developing PJK or other adjacent segment diseases. The telescoping rod may be implanted as a prophylactic and used if needed to extend the length for pain relief. An example of the telescoping rod is shown in FIG. 6. In this particular embodiment, the telescoping spinal rod 255 comprises a rod magnet 260 configured to rotate when exposed to a spinning magnetic field and cause the telescoping spinal rod 255 to either extend or collapse depending on the direction of the spinning magnetic field. The rod magnet 260 may be a cylindrical permanent magnet (such as a ferrimagnet), but may be another type of magnet. The telescoping rod may include a first elongate element 265 containing a cavity 270, into which fits a second elongate element 275. There may be a dynamic seal between the first 265 and second elongated elements 275, to ensure that no bodily fluids enter the telescoping rod. A thrust bearing may be included to reduce friction between the spinning magnetic element and the housing. The second elongate element 275 can have an internally threaded region 280 that is engaged to a lead screw 285 coupled to rotate when the rod magnet 260 rotates, and comprising an externally threaded region 290, such that rotation of the lead screw 285 causes the second elongate element 275 to translate along the longitudinal direction relative to the first elongate element 265. Thus, when the magnet 260 rotates, the lead screw 285 can also rotate. The threaded interface between the lead screw 285 and the second elongated element 275 can then cause the second elongated element 275 to translate, with the translational direction being dependent upon the rotational direction of the magnet 260. The threads on the internally threaded region 280 of the first elongate element 265 may be integral, or they may be on the inner surface of another structure, such as a threaded nut.

Whenever the adjustable tensioner is actuated by the rotation of a magnet 120, as a safety precaution, a magnetic immobilization plate 295 may be positioned sufficiently close to the rotatable magnet 120 to cause the rotatable magnet 120 to adhere to the immobilization plate 295 in the absence of a strong external magnetic field. The magnetic immobilization plate 295 can hold the rotating magnet 120 in position, preventing it from rotating, until a magnetic field with a strength above a certain threshold is applied. Like the rotating magnet 120, the immobilization plate may be constructed from a suitable magnetic material, such as a ferromagnetic material. The immobilization plate may be used on its own, or in combination with a locking mechanism 195 as described above.

Methods of using the vertebral fixation system 5 to fix the relative positions of a first vertebra and a second vertebra in a subject are provided herein. In some embodiments, the method comprises anchoring a first bone anchor 10 to the first vertebra, the first bone anchor 10 comprising a first bone fastener 15 attached to a first rod housing 20; seating a rigid spinal rod 25a in the first rod housing 20 to restrict translation of the rigid spinal rod 25a relative to the first bone anchor 10; anchoring a second bone anchor 30 to the second vertebra, the second bone anchor 30 comprising a second bone fastener 33 attached to a second rod housing 35; seating the first rigid spinal rod 25a in the second rod housing 35 to restrict translation of the rigid spinal rod 25a relative to the second bone anchor 30; connecting a compressible spinal connector to the second bone anchor 30, the compressible spinal connector comprising a modulation mechanism for modulating at least one of the tension on the compressible spinal connector or the resistance to compression of the compressible spinal connector, wherein said modulation occurs in response to a remote signal; anchoring the compressible spinal connector to a third vertebra in the subject; and transmitting the remote signal to the modulation mechanism post-operatively, to cause said modulation to occur. The vertebral fixation system may have any of the components and arrangements described above. The compressible spinal connector can be any described as suitable for the system above, including any of the described embodiments of the tether assembly, dampening rod, and telescoping rod. An example of an external adjustment device 155 that can be used to non-invasively drive the modulation mechanisms described herein is shown in FIG. 9. The external adjustment device 155 is configured for placement on or adjacent to the skin of the subject and appropriately aligned with the magnet to be activated, and includes at least one drive magnet 230a, 230b configured for rotation. The external adjustment device 155 may further include a motor configured to rotate the magnet(s), whereby rotation of the drive magnet(s) of the external adjustment device 155 effectuates rotational movement of one or more magnets (e.g., rotatable magnet in the turnbuckle, magnetic set screw, etc.). As shown in FIG. 9, the external adjustment device 155 may have two magnets (230a, 230b). The two magnets (230a, 230b) may be configured to rotate at the same angular velocity. They may also be configured to each have at least one north pole and at least one south pole (i.e., a dipole magnet), and the external adjustment device 155 is configured to rotate one drive magnet 230a and the other drive magnet 230b such that the angular location of the at least one north pole of the first drive magnet 230a is substantially equal to the angular location of the at least one south pole of the second drive magnet 230b through a full rotation of the first 230a and second 230b drive magnets. More complex systems involving quadrupole and multipole drive magnets are also contemplated, as is the use of one or more electromagnets.

The foregoing description illustrates and describes the processes, machines, manufactures, compositions of matter, and other teachings of the present disclosure. Additionally, the disclosure shows and describes only certain embodiments of the processes, machines, manufactures, compositions of matter, and other teachings disclosed, but, as mentioned above, it is to be understood that the teachings of the present disclosure are capable of use in various other combinations, modifications, and environments and is capable of changes or modifications within the scope of the teachings as expressed herein, commensurate with the skill and/or knowledge of a person having ordinary skill in the relevant art. The embodiments described hereinabove are further intended to explain certain best modes known of practicing the processes, machines, manufactures, compositions of matter, and other teachings of the present disclosure and to enable others skilled in the art to utilize the teachings of the present disclosure in such, or other, embodiments and with the various modifications required by the particular applications or uses. Accordingly, the processes, machines, manufactures, compositions of matter, and other teachings of the present disclosure are not intended to limit the exact embodiments and examples disclosed herein. Any section headings herein are provided only for consistency with the suggestions of 37 C.F.R. § 1.77 and related laws or otherwise to provide organizational queues. These headings shall not limit or characterize the invention(s) set forth herein.

While preferred embodiments of the present invention have been described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will be apparent to those skilled in the art without departing from the invention. Furthermore, it shall be understood that all aspects of the invention are not limited to the specific depictions, configurations, or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations, or equivalents. It is intended that the following claims define the scope of the invention and that methods and structures within the scope of these claims and their equivalents be covered thereby.

What is claimed is:

1. A system for spinal fixation comprising:
   a first bone anchor configured to be anchored to a first vertebra of a subject, the first bone anchor comprising a first bone fastener attached to a first rod housing;
   a second bone anchor configured to be anchored to a second vertebra of the subject, the second bone anchor comprising a second bone fastener attached to a second rod housing;
   a third bone anchor configured to be anchored to the first vertebra, the third bone anchor comprising a third bone fastener attached to a third rod housing;
   a fourth bone anchor configured to be anchored to the second vertebra, the fourth bone anchor comprising a fourth bone fastener attached to a fourth rod housing;
   a first rigid spinal rod seated in the first rod housing and the second rod housing;
   a second rigid spinal rod seated in the third rod housing and the fourth rod housing,
   a first flexible tether connected to each of the first rigid spinal rod and the second rigid spinal rod and configured to be wrapped at least partially around a third vertebra of the subject to exert tension between the third vertebra and the first and second rigid spinal rods;
   a second flexible tether configured to encircle a portion of the third vertebra and a portion of a fourth vertebra of the subject; and
   an adjustable tensioner coupled to the first rigid spinal rod, the second rigid spinal rod, and one or both of the first and second flexible tethers, the adjustable tensioner comprising a magnet that rotates in response to an external force.

2. The system of claim 1, wherein the adjustable tensioner further comprises a tension modulation mechanism configured to convert rotation of the magnet to a change in tension on one or both of the first and second flexible tethers.

3. The system of claim 2, wherein the tension modulation mechanism comprises a threaded first end coupler and a second end coupler, wherein the magnet is coupled to the threaded first end coupler such that the threaded first end coupler rotates about its longitudinal axis in response to rotation of the magnet.

4. The system of claim 1, wherein the adjustable tensioner comprises a spool about which one or both of the first and second flexible tethers is wound, and wherein rotation of the magnet drives rotation of the spool.

5. The system of claim 4, wherein the spool further comprises a locking mechanism configured to maintain tension on one or both of the first and second flexible tethers engaged with the spool.

6. The system of claim 4, wherein the spool further comprises a locking mechanism that comprises a set screw configured to inhibit rotation of the spool.

7. The system of claim 1, wherein one or both of the first and second flexible tethers comprises a non-absorbable biocompatible material.

8. The system of claim 1, wherein the external force comprises an electromagnetic signal or a spinning magnetic field.

9. The system of claim 1, further comprising a cross connector unit fastened to the first and second rigid spinal rods.

10. The system of claim 9, wherein the cross connector unit is configured to rigidly engage with the first and second rigid spinal rods.

11. The system of claim 9, wherein the cross connector unit further comprises a first rod connector attached to the first rigid rod, a second rod connector attached to the second rigid rod, and one or more support arms extending from a respective one of the first and second rod connectors for attaching to a housing of the adjustable tensioner.

12. A system for spinal fixation comprising:
    a first bone anchor configured to be anchored to a first vertebra of a subject, the first bone anchor comprising a first bone fastener attached to a first rod housing;
    a second bone anchor configured to be anchored to a second vertebra of the subject, the second bone anchor comprising a second bone fastener attached to a second rod housing;
    a third bone anchor configured to be anchored to the first vertebra, the third bone anchor comprising a third bone fastener attached to a third rod housing;

a fourth bone anchor configured to be anchored to the second vertebra, the fourth bone anchor comprising a fourth bone fastener attached to a fourth rod housing;

a first rigid spinal rod seated in the first rod housing and the second rod housing;

a second rigid spinal rod seated in the third rod housing and the fourth rod housing, a first flexible tether connected to each of the first and second rigid spinal rods and configured to be wrapped at least partially around a third vertebra of the subject to exert tension between the third vertebra and the first and second rigid spinal rods;

a second flexible tether configured to encircle a portion of the third vertebra and a portion of a fourth vertebra of the subject;

an adjustable tensioner coupled to the first rigid spinal rod, the second rigid spinal rod, and one or both of the first and second flexible tethers, the adjustable tensioner comprising a magnet that rotates in response to a spinning magnetic field; and a cross connector unit fastened to the first and second rigid spinal rods.

13. The system of claim 12, wherein the cross connector unit is configured to rigidly engage with and extend between the first and second rod connectors.

14. The system of claim 12, wherein the cross connector unit further comprises a support arm attached to a housing of the adjustable tensioner.

* * * * *